(12) United States Patent
Monk et al.

(10) Patent No.: US 7,926,119 B2
(45) Date of Patent: Apr. 19, 2011

(54) IMPACT-PROTECTION SLIP-PLATE STRUCTURE AND METHODOLOGY

(75) Inventors: Russell A. Monk, Salem, OR (US); Jodi Maxey-Shearman, Salem, OR (US)

(73) Assignee: High Impact Technology, L.L.C., Tigard, OR (US)

( * ) Notice: Subject to any disclaimer, the term of this patent is extended or adjusted under 35 U.S.C. 154(b) by 1014 days.

(21) Appl. No.: 11/801,452

(22) Filed: May 9, 2007

(65) Prior Publication Data

US 2007/0265556 A1 Nov. 15, 2007

Related U.S. Application Data

(60) Provisional application No. 60/800,476, filed on May 12, 2006.

(51) Int. Cl.
*A41D 13/00* (2006.01)
(52) U.S. Cl. .............................................................. 2/24
(58) Field of Classification Search .................. 2/16, 24, 2/455, 62, 23, 465, 267, 268
See application file for complete search history.

(56) References Cited

U.S. PATENT DOCUMENTS

| 4,455,686 | A  | * | 6/1984  | Zide ..................................... 2/23 |
| 5,781,935 | A  | * | 7/1998  | Bassett et al. ...................... 2/455 |
| 6,317,889 | B1 | * | 11/2001 | Reilly et al. ......................... 2/24 |
| 6,464,480 | B2 | * | 10/2002 | Fenocchi et al. ............. 418/55.6 |
| 7,168,104 | B2 | * | 1/2007  | Tobergte ........................... 2/459 |
| 7,188,370 | B2 | * | 3/2007  | Bevier ............................... 2/22 |

* cited by examiner

*Primary Examiner* — Tejash Patel
(74) *Attorney, Agent, or Firm* — Jon M. Dickinson, Esq.; Robert D. Varitz, Esq.

(57) ABSTRACT

Impact-protection slip-plate structure and methodology involving (a) a generally planar, plural-layer, outside-jacketed, shock-absorbing barrier assembly positionable relative to the human anatomy in a location adjacent a body zone to be protected, and (b), disposed within that assembly, a generally planar, friction-reduced slip-plate organization including a pair of facially confronting, generally planar slip-plate substructures disposed on opposite sides of a friction-reduced slip plane, responsive to an impact occurring along a line which lies at a angle other than normal to the slip plane to produce relative-motion impact-initiated slippage of the two slip sub-structures with respect to one another along opposite sides of the slip plane.

12 Claims, 1 Drawing Sheet

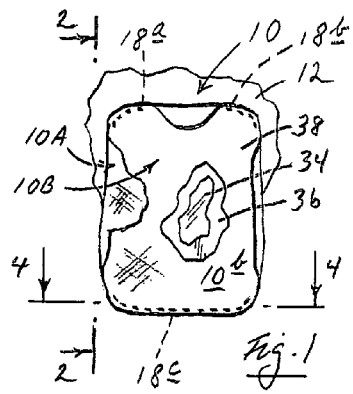
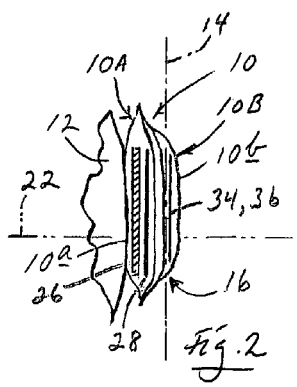
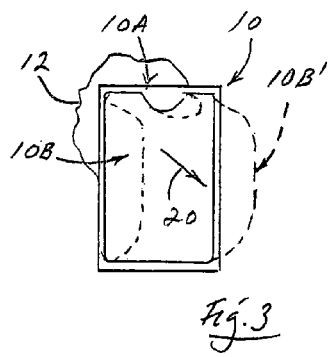
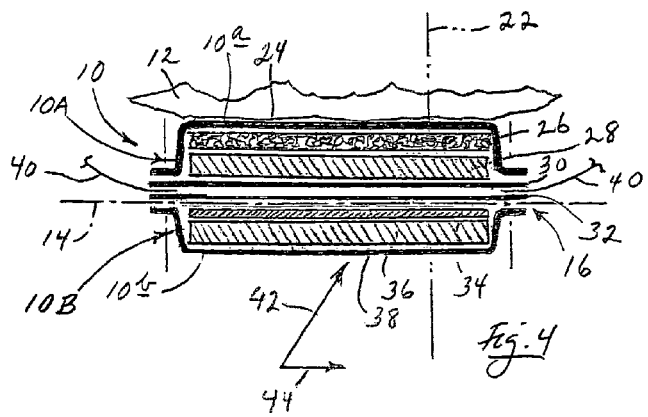
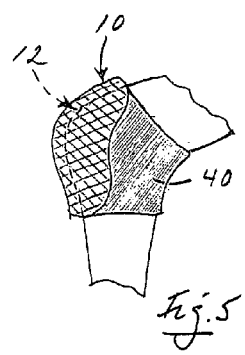
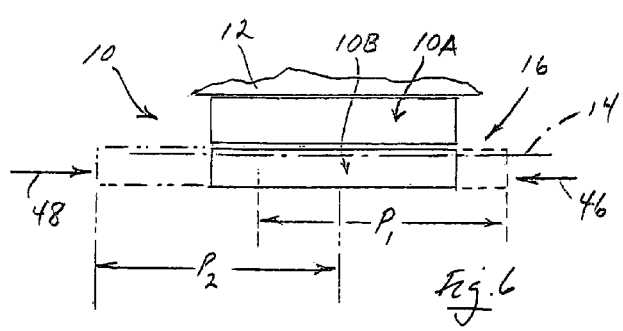
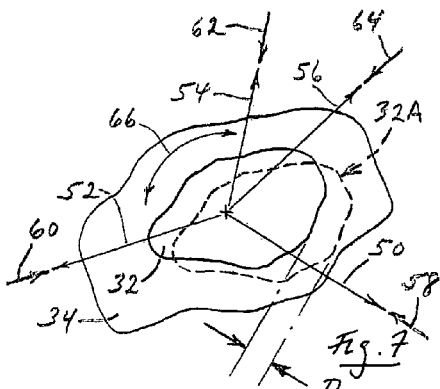
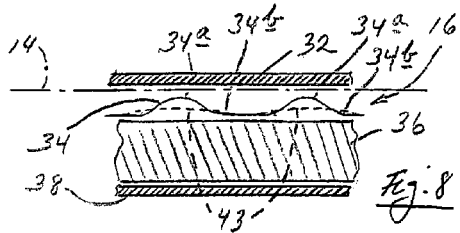

IMPACT-PROTECTION SLIP-PLATE STRUCTURE AND METHODOLOGY

CROSS-REFERENCE TO RELATED APPLICATION

The application claims priority to the filing date May 12, 2006 of U.S. Provisional Patent Application Ser. No. 60/800, 476, covering an invention entitled "Slip-Plate Body Armor and Method". The entire disclosure content of that prior-filed, currently pending provisional application is hereby incorporated herein by reference.

BACKGROUND AND SUMMARY OF THE INVENTION

This invention pertains to body armor for human anatomical impact-injury mitigation. More specifically, the invention pertains to body armor and methodology in the forms of impact-protection slip-plate structure and methodology which utilize, along with appropriate, viscoelastic, acceleration-rate-sensitive, shock-cushioning action, the mechanism of friction-reduced lateral slip between a pair of confronting, generally planar slip-plate sub-structures (collectively called herein a slip-plate organization) to isolate from the anatomy lateral, as distinguished from normal, forces (force vectors) which often attend anatomical impact events.

While there are many applications for use of the present invention, a preferred and best mode embodiment thereof, and a preferred manner of implementing the same, along with certain proposed modified forms of the invention, are described herein illustratively in the use field of impact sports, such as the sport of football. Other recognized use areas include (a) helmets, (b) shoulder, elbow, thigh and chest padding, (c) protective padding required for other activities, seating cushions and backrests in vehicles and the like, and so on.

Much work has been done over the years to improve body armor (i.e., body protection structure) which is intended to protect the anatomy against injury encountered in impact events such as those which are experience by football players during a game, as well as to protect various anatomical zones of those who are engaged in other activities, events, and settings where a shock impact might be experienced. The usual and conventional approach for addressing impact injury involves the provision of an armoring structure which is designed principally to minimize the amount of "normal-direction (i.e., normal-vector)" shock delivered to the anatomy during an impact. The term "normal-direction" refers to that vector of an impact shock event which is directed substantially perpendicularly relative to the impacted portion or zone of the anatomy.

It turns out that many impact events are characterized not only by a normal force vector, but also by a lateral force vector, due to the fact that the specific direction of impact often lies along a line inclined at an angle other than a right angle relative to the impacted zone of the anatomy. From what has just been said above about the conventional approach toward dealing with such a impact, it is clear that conventional wisdom directs attention substantially solely to the normal impact vector, rather than to what turn out frequently be the more serious impact vector, namely, that which defines a lateral impact and shock force applied to the anatomy.

The present invention—via its associated structure and methodology—directly focuses upon this largely unaddressed area of impact-injury mitigation, and does so, as will be seen from the detailed description which follows below, through utilization of an intentionally designed, friction-reduced slip-plate structure which effectively prevents lateral force vectors from being delivered to the anatomy. The invention does this through confining the response-result of such an impact vector substantially to innocuous, returnable lateral slip between a pair of specially arranged slip-plate components (called slip-plate sub-structures) which lie collaboratively intermediate an impact event and a protected zone in the anatomy, thus isolating the anatomy from the lateral characteristics of such an impact.

Preferably, this approach is accompanied by a mechanism and a methodology which involve nominally yieldably biasing the relative-motion slip-plate components into a normal non-slipped position, or relationship, with respect to one another, which biasing operates, immediately following an impact-initiated slip event, to return the two, relative-motion slip-plate components from the thereby-produced slipped condition to the mentioned, nominal, non-slipped positional relationship.

The slip-plate structure of the preset invention includes, in addition to the slip-plate structure just generally discussed, appropriate shock-absorbing cushioning structure which deals with normally-directed impact shock-force vectors.

A further inclusion in the mechanism of the invention is a layer arrangement (two somewhat different layers in the preferred embodiment of the invention specifically described herein) of a so-called three-dimensional mesh knit spacer-fabric which functions to provide, along with reversible, collapse-based shock-absorption, cooling, air-flow breathability in a region of the slip-plate structure of the invention which lies most closely adjacent the anatomy when that structure is worn for use.

Others of the various important features and advantages which are offered by the structure and methodology of the present invention will become more fully apparent understood as the detailed description thereof which follows below is read in conjunction with the accompanying drawings.

DESCRIPTIONS OF THE DRAWINGS

FIG. 1 is a simplified, outer-side plan view of a preferred and best mode embodiment of the impact-protection slip-plate structure of the present invention, with the subject slip-plate structure illustrated disposed worn on the front of a user's knee (shown fragmentarily), but with conventional, elastic-band-style knee-attaching structure omitted from this figure. Such attaching structure is shown in other ones of the drawing figures.

FIG. 2 is a side elevation taken generally along the line 2-2 in FIG. 1.

FIG. 3 is a stylized, schematic, frontal view, somewhat like that presented in FIG. 1, illustrating the manner in which perimetral, or edge, connections that exist between a pair of bag-layer sub-assemblies in the structure of FIGS. 1 and 2 accommodate a limited amount of returnable, lateral relative motion between these two sub-assemblies.

FIG. 4 is a simplified, schematic cross-section of the slip-plate structure of FIGS. 1 and 2, taken generally along the line 4-4 in FIG. 1.

FIG. 5 is a simplified and fragmentary lateral side illustration of the slip-plate structure of FIGS. 1, 2 and 4 shown, as indicated above in the description of FIG. 1, worn on the knee of a user (herein, a football player).

FIG. 6 is simplified, stylized, fragmentary, schematic, illustration, taken generally from the point of view of FIG. 4, showing, in two different slip-plate-component-moved conditions, two instances of the slip-plate impact-protection action which is offered by the structure of the present invention.

FIG. 7 is a simplified, stylized, fragmentary, schematic plan view also illustrating aspects of the slip-plate impact-protection action of the present invention.

FIG. 8 is a fragmentary, enlarged view picturing two different operative conditions of a modified form of the invention, with this view being taken generally from the point of view of FIG. 4, showing a modification in friction-reducing structure located near the lower portion of FIG. 4.

In these drawing figures, components are not drawn to scale. Additionally, many, specific structural details of these components are not pictured, inasmuch as such details, per se, form no part of the present invention.

DETAILED DESCRIPTION OF THE INVENTION

In this detailed description of the invention, particular drawing figures, not necessarily in ascending numeric order, will be mentioned and drawn into the discussion as and where they become relevant and useful to the flow of description.

In FIG. 1, the structural organization of a preferred and best mode embodiment of the present invention, referred to as impact-protection slip-plate structure, and sometimes simply as slip-plate structure, is illustrated generally and schematically at 10. Structure 10, a nominally generally planar structure (which is also referred to herein as a generally planar, plural-layer, outside-jacketed, shock-absorbing barrier assembly) is, as just parenthetically stated, a plural-layer structure, wherein each layer, while easily flexed to fit snuggly, comfortably and in topographical conformance with the anatomy, such as with the knee, or anatomical body zone, 12 of a football player as is illustrated in FIGS. 1-6, inclusive, is also nominally generally individually planar in nature.

In broad terms, the slip-plate structure, and associated barrier assembly, of the invention, with specific reference to the embodiment thereof which is principally discussed herein, include inner (anatomy-side) and outer (impact-side), generally planar bag-layer sub-assemblies 10A, 10B, respectively, with respect to which a slip plane 14 extends, as shown, through, and generally in the plane of, outer sub-assembly 10B. Sub-assembly 10A is also referred to herein as a first bag-layer sub-assembly, and sub-assembly 10B as a second bag-layer sub-assembly. Each of these two sub-assemblies includes an outside bag enclosure formed of suitable fabric-layer materials, with each bag enclosure, still to be more fully described, enclosing, as contents, various other components of the invention which will also be more fully discussed shortly. Slip plane 14 specifically extends through and is associated with what is referred to herein as a slip-plate organization generally shown at 16 in FIGS. 2, 4, 6 and 8.

The two bag enclosures preferably, though not necessarily in all applications, are attached to one another near their perimeters in a manner which permits, to their associated bag-layer sub-assemblies, a limited amount of returnable, lateral relative motion shifting. In the cases of sub-assemblies 10A, 10B, as shown designed for use with respect to a knee, sewn, or conventional peel-and-stick adhesive, attachments are provided at the three locations shown generally by dashed lines 18a, 18b, 18c in FIG. 1. These attachments, given the specific materials (still to be described) chosen to form the two bag enclosures, permit what has been referred to hereinabove as returnable, relative lateral motion in an infinite number of directions. FIG. 3, at 10B', illustrates one such condition of relative-motion returnable shifting of sub-assembly 10B relative to sub-assembly 10A in the direction of arrow 20. The concept of "returnable" is expressed to reflect the fact that certain elastomeric materials are here involved in the structures of the two bag-layer sub-assemblies, which materials load like springs during lateral shifting to furnish appropriate "return" forces.

Such motion permission is especially useful in settings where the invention is designed and configured to furnish protection to an anatomical joint, such as the knee or the elbow. In such a setting, this motion permission offers useful freedom of flexing in such a joint.

Continuing with a description of the structural features of the invention embodiment so far described herein, progressing outwardly (to the right in FIG. 2, and downwardly in FIG. 4), as along an imaginary, dash-double-dot transit line 22 shown in FIGS. 2 and 4, through structure 10, from what is its inner, anatomy-facing side 10a (see especially FIG. 2) as defined by bag-layer sub-assembly 10A, to what is its outer, impact-facing side 10b as defined by bag-layer sub-assembly 10B, there are eight material layers, each being generally planar in nature.

These layers include: (a) a first, outer, mesh knit spacer-fabric material layer 24 having a thickness herein of about 1/16-inches; (b) a second, inner, mesh knit spacer-fabric material layer 26 having a thickness herein of about 1/4-inches, and together with mesh layer 24 constituting a mesh knit spacer-fabric arrangement; (c) an acceleration-rate-sensitive, viscoelastic foam-material, shock-absorbing, cushioning-material layer 28 having a thickness herein of about 3/16-inches, preferably formed of the material sold under the trademark and name PORON® Performance Urethane, respectively, made by Rogers Corporation in Woodstock, Conn.; (d) a layer 30 formed herein of an elastomeric, stretchy fabric, such as the material sold under the trademark LYCRA®, with a thickness of about 0.015-inches; (e) another layer 32 also formed herein of an elastomeric, stretchy fabric, such as the material sold under the trademark LYCRA®, also possessing a thickness of about 0.015-inches; (f) a layer 34 formed of a low-coefficient-of-friction, friction-reducing material, such as the material sold under the trademark TEFLON®, or a friction-reducing material such as UHMW plastic, preferably with a thickness herein of about 0.01-inches; (g) another layer 36 formed preferably of the same cushioning PORON® material with about the same thickness which characterizes layer 28; and (h) yet another stretchy elastomeric layer 38 which is essentially the same in nature and structure as layers 30, 32.

Layers 34, 36 are preferably surface-bonded to one another. In FIG. 2, for space-saving reasons, layers 34, 36 are shown by a single dark line. The mentioned mesh knit spacer-fabric layers are preferably formed of such conventional material which is made by Gehring Textiles, Inc. in Johnsonville, N.Y. Outer mesh layer 24, together with elastomeric layer 30, form the previously mentioned bag enclosure which is associated with bag-layer sub-assembly 10A. Similarly, elastomeric layers 32, 38 form the previously mentioned bag enclosure which is associated with bag-layer sub-assembly 10B. It is the elastomeric stretchiness in layers 32, 38 which permits the relative-motion slippage between the two sub-assemblies as pictured illustratively in FIG. 3.

Friction-reducing layer 34, together with the confronting and engaging central planar portion of elastomeric layer 32, are referred to herein as slip-plate sub-structures, and together form previously mentioned slip-plate organization 16. Collectively, the respective expanses of elastomeric layers 32, 38, including that portion of layer 32 which also form part of previously mentioned slip-plate organization 16, constitute a slip-loadable biasing structure in the invention. This biasing structure tends to hold the two slip-plate sub-structures in what is referred to herein as a nominal, non-slipped relationship with respect to one another on the opposite sides of slip plane. This nominal positional relationship is shown in FIGS. 2, 4, and 6, and is also shown in FIG. 7 in solid lines.

The basic perimetral shape and size of structure 10 is purely a matter of designer choice, and is established in accordance with the specific use-application intended for it. For example, in the knee-protecting illustration provided herein, structure 10 might be somewhat ovate in perimetral outline, with a length of about 10-12-inches, and a width of about 6-8-inches. The overall thickness of structure 10 may be varied to suit different use-applications, with thickness variations being introduced by thickness variations in one or more of the several material layers described above. For examples, inner mesh knit spacer-fabric layer 26 might have a thickness, typically lying in the range of about ¼-inches to about ⅜-inches, or, this layer might be omitted entirely for certain applications. Cushioning layers 28, 36 might typically have thicknesses lying in the range of about 3/16-inched to about ¼-inches. Friction-reducing layer 34 might typically have a thickness lying in the range of about 0.005-inches to about 0.1-inches.

As by sewing, or by the use of a conventional peel-and-stick adhesive, the individual perimeters of the two bag-layer sub-assemblies are appropriately closed via slight lateral envelope extensions of layers 24, 30, 32 and 34.

In the particular embodiment of the invention which has so far been described, structure is elastically bound removeably to the knee by means of a conventional elastomeric band, such as the band shown at 40 in FIGS. 4 and 5.

FIG. 8 in the drawings illustrates a modified form of the invention wherein friction-reducing layer 34 is formed with subtle, slightly out-of-plane islands and valleys, such as the islands shown at 34a, and the valleys shown at 34b. The islands may preferably take the forms either of small, spaced mounds, or of elongate ridges. When an impact strikes, these islands tend, elastically, and therefore reversibly, to flatten, as illustrated in FIG. 7 by dashed lines 43. This flattening behavior dissipates impact energy, and thus assists in impact shock mitigation relative to the anatomy.

Structure 10 performs, in accordance with slip-plate-action practice of the present invention, in a manner which, from the above structural description of the invention, should be immediately apparent. FIGS. 6 and 7 illustrate such slip-plate action with respect to a lateral-vector-component-containing shock impact like that illustrated by vector arrows 42, 44 in FIG. 1. Arrow 44, of course represents such a lateral vector component.

Impact of such a shock event is taken initially by the impact side of structure 10. With receipt of this shock impact, the lateral vector component therein causes the central expanse portion of layer 32 to slide easily in slip plane 14 with little frictional resistance over and relative to the facing surface of friction-reducing layer 34, and in a direction relating to the direction of vector 44. Such slipping effectively decouples the lateral force vector from the protected knee, leaving bag-layer sub-structure 10A substantially un-moved, and thus providing remarkable diminution, almost to zero, of the impact lateral characteristic which reaches the knee. Such slipping also produces a related stretching and tensing in layer 32, and it is this stretching and tensing which generates a restoring force which, at the conclusion of the related impact event, causes a return of the overall slip-plate assembly to return to it nominal, non-slipped condition.

Slipping-related relative motion of the slip-plate sub-structures may take place (a) along a straight line, (b) along a curved line (which may be either rotational or orbital), or (c) along a complex "combination" line. FIG. 6, in dashed and dash-double-dot lines, respectively, shows two, different, opposite-direction conditions of slippage, labeled $P_1$ and $P_2$. Related restoring forces are represented by arrows 46, 48.

FIG. 7 shows, by linear arrows 50, 52, 54, 56, four different conditions of slippage between slip-plate sub-structures, or layers, 32, 34. One of these four conditions of slippage, and namely that condition which relates to arrow 52, shows, in dashed lines, a fragment of sub-structure 32 slipped a distance D relative to a fragment of sub-structure 34 to a slipped-to location labeled 32A. Restoring forces exerted by the biasing structure of structure 10A in relation to slip-illustrating arrows 50, 52, 54, 56 are pictures by reversely-directed arrows 58, 60, 62, 64, respectively. A curved, double headed arrow 66 represents curved-line slipping, as by rotation or orbital motion. As was mentioned earlier herein, complex motion slipping may also take place.

Layers 24, 26, 28, 36 provide shock mitigation relative to the normal-direction vector of a shock impact. Layers 24, 26 additionally introduce air-flow cooling in the region immediately adjacent the protected zone of the anatomy.

While the embodiment of the invention described herein, including the modification shown in FIG. 8, contemplates the presence of two bag enclosures whose facing sides are defined by elastomeric fabric layers 30, 32, in certain applications, a single bag enclosure alone could be employed, with layer 30 omitted, and layers 26, 38 then defining the outer jacket of a resulting, single bag enclosure.

From the above discussion, one can express the methodology of the invention as being a method utilizing, in a multi-layered shock-absorbing structure, controlled, friction-reduced, internal component lateral slippage as a mechanism for protecting a human anatomical zone from lateral-vector shock-impact injury, with this method including (a) placing such a structure between that zone and an oncoming shock impact possessing such a vector so that the structure directly receives the shock impact, (b) by such placing, on receipt of the shock impact, and in addition to shock-cushioning any normal-vector characteristic of that impact, producing internal component lateral slip within the shock-absorbing structure, and (c) by such producing, substantially isolating the mentioned anatomical zone from any impact-initiated lateral shock and motion, and thereby furnishing lateral-vector shock-impact protection from injury for the subject anatomical zone.

While a preferred form of the invention, and one modification thereof, as well as a preferred methodology associated with the invention, have been illustrated and described herein, other variations may be made if desired which are anticipated will come within the scope of the following claims.

We claim:

1. Impact-protection slip-plate structure comprising
a generally planar, plural-layer, outside-jacketed, shock-absorbing barrier assembly positionable relative to the human anatomy in a location adjacent a body zone to be protected, and
disposed within said assembly, a generally planar, friction-reduced slip-plate organization including a pair of facially confronting, generally planar slip-plate sub-structures disposed on opposite sides of a friction-reduced slip plane, responsive to an impact occurring along a line which lies at an angle other than normal to said slip plane to produce relative-motion impact-initiated slippage, along a path taken from the group of paths consisting of straight and curved, of the two slip sub-structures with respect to one another along opposite sides of the slip plane, said barrier assembly further including slip-loadable biasing structure operatively associated with said slip-plate sub-structures, (a) operable nominally to hold said sub-structures yieldably in a nominal, non-slipped positional relationship with respect to one another on opposite sides of said slip plane, (b) constructed to accommodate a limited amount of the mentioned impact-initiated, relative-motion slippage between the sub-structures, and (c), further operable, following the occurrence of such slippage, to urge the two slip-plate sub-structures relatively to return to the mentioned nominal, non-slipped positional relationship.

2. The slip-plate structure of claim 1, wherein said two slip-plate sub-structures include, on one side of said slip plane, a generally planar layer of a friction-reducing material, and on the other side of the slip plane, a portion of said biasing structure, which portion takes the form of a generally planar layer of a stretchable, elastomeric fabric material.

3. The slip-plate structure of claim 2, wherein said friction-reducing material includes plural, out-of-plane, into-and-out-of-plane-deformable, island protrusions.

4. The slip-plate structure of claim 2, wherein said barrier assembly further includes, adjacent said slip-plate organization, a generally planar layer of viscoelastic, acceleration-rate-sensitive, shock-absorbing cushioning material disposed on the opposite side of said friction-reducing material relative to said layer portion of said biasing structure.

5. The slip-plate structure of claim 1, wherein said barrier assembly has an impact-facing side and an anatomy-facing side, and said cushioning material is disposed toward said impact-facing side relative to said friction-reducing material.

6. The slip-plate structure of claim 5, wherein said barrier assembly further includes a generally planar layer arrangement of mesh knit spacer-fabric disposed toward its said body-facing side, with said slip-plate organization being disposed toward the barrier assembly's said impact-facing side relative to said spacer-fabric.

7. The slip-plate structure of claim 6, wherein said barrier assembly further includes a second generally planar layer of viscoelastic, acceleration-rate-sensitive, shock-absorbing cushioning material disposed adjacent said mesh knit spacer-fabric arrangement and within a bag enclosure formed, at least in part, of an expanse of stretchable, elastomeric fabric material, and wherein said second cushioning material, said mesh knit spacer-fabric arrangement, and said bag enclosure collectively form a first, generally planar bag-layer sub-assembly which is positioned on said body-facing side of said barrier assembly.

8. The slip-plate structure of claim 7, wherein said layer arrangement of mesh knit spacer-fabric includes outer and inner layers.

9. The slip-plate structure of claim 8, wherein said outer layer of mesh knit spacer-fabric together with said fabric-material expanse form said bag enclosure.

10. The slip-plate structure of claim 9, wherein said layer portion of said biasing structure cooperates with a second, like layer portion of a stretchable, elastomeric material to form another bag enclosure encompassing, as contents, (a) said friction-reducing material, and (b) said first-mentioned layer of cushioning material, thus to form, along with said contents, a second, generally planar bag-layer sub-assembly.

11. The slip-plate structure of claim 10, wherein said two layer portions of elastomeric material cooperate to form said biasing structure.

12. The slip-plate structure of claim 10, wherein said first bag-layer sub-assembly is disposed on said anatomy-facing side of said barrier assembly, said second bag-layer sub-assembly is disposed on said impact-facing side of the barrier assembly, and said two bag-layer sub-assemblies have edges which are connected in a manner allowing for limited, returnable, lateral relative motion with respect to one another.

* * * * *